(12) United States Patent
Bresin Hanson et al.

US008592485B2

(10) Patent No.: US 8,592,485 B2
(45) Date of Patent: Nov. 26, 2013

(54) METHODS AND PHARMACEUTICAL COMPOSITIONS FOR TREATING THE ANIMAL CENTRAL NERVOUS SYSTEM FOR PSYCHIATRIC DISORDERS

(75) Inventors: Leah Ranae Bresin Hanson, Vadnais Heights, MN (US); William H. Frey, II, White Bear Lake, MN (US)

(73) Assignee: HealthPartners Research Foundation, Minneapolis, MN (US)

( * ) Notice: Subject to any disclaimer, the term of this patent is extended or adjusted under 35 U.S.C. 154(b) by 214 days.

(21) Appl. No.: 13/161,934

(22) Filed: Jun. 16, 2011

(65) Prior Publication Data

US 2011/0311654 A1 Dec. 22, 2011

Related U.S. Application Data

(60) Provisional application No. 61/355,626, filed on Jun. 17, 2010.

(51) Int. Cl.
*A61K 31/13* (2006.01)
*A61K 31/131* (2006.01)
*A61K 31/16* (2006.01)

(52) U.S. Cl.
USPC .......................................... 514/616; 514/645

(58) Field of Classification Search
USPC .................................................. 514/616, 645
See application file for complete search history.

(56) References Cited

U.S. PATENT DOCUMENTS

| | | |
|---|---|---|
| 2005/0031651 A1 | 2/2005 | Gervais et al. |
| 2007/0092500 A1 | 4/2007 | Frey, II et al. |
| 2008/0305077 A1 | 12/2008 | Frey, II et al. |
| 2009/0118278 A1 | 5/2009 | Forster et al. |

OTHER PUBLICATIONS

M. J. Miller, "Synthesis and Therapeutic Potential of Hydroxamic Acid Based Siderophores and Analogues," Chem. Rev., 1989, vol. 89, pp. 1563-1564, and 1577.*
Se-Hoon Shim et al. "Association between glycogen synthase kinase-3b gene polymorphisms and attention deficit hyperactivity disorder in Korean children: A preliminary study" Progress in Neuro-Psychopharmacology & Biological Psychiatry 2012, 39, pp. 57-61.*
Richard S. Jope and Myoung-Sun Roh, "Glycogen Synthase Kinase-3 (GSK3) in Psychiatric Diseases and Therapeutic Interventions," Curr. Drug Targets, Author Manuscript available in PMC Apr. 10, 2007, accessed online at http://www.ncbi.nlm.nih.gov/pmc/articles/PMC1850891/ on Jul. 19, 2013.*
Gould et al., "Glycogen Synthase Kinase-3: A Target for Novel Bipolar Disorder Treatment," Jan. 31, 2004. The Journal of Clinical Psychiatry, vol. 65, Is. 1; p. 10-21; especially abstract; p. 13, col. 2, para 3; p. 15, col. 1, para 4 to col. 2, para 1; p. 17, col. 1, para 2.
Qu et al., Promotion of osteogenesis through b-catenin signaling by desferrioxamine, May 31, 2008. Bio chemical and Biophysical Research Communications, vol. 370, Is. 2, p. 332-338; especially abstract; p. 334, col. 2, para 1.
Gould et al., "Beta-Catenin Overexpression in the Mouse Brain Phenocopies Lithium-Sensitive Behaviors," (2007). Neuropsychopharmacology, vol. 32 p. 2173-2183, entire document.

* cited by examiner

*Primary Examiner* — Jmes H. Alstrum-Acevedo
(74) *Attorney, Agent, or Firm* — Winthrop & Weinstine, P.A.

(57) ABSTRACT

The present invention comprises methods and pharmaceutical compositions for intranasal delivery of effective amounts of DFO directly to the CNS, in particular the brain treatments that inhibit GSK3b in patients with psychiatric disorders including, but not limited to, bipolar disorder, depression, ADHD and schizophrenia. In addition a treatment composition is disclosed which comprises DFO and in certain embodiments combines DFO with one or more of the psychotropic drug types, i.e., antipsychotics, mood stabilizers and antidepressants. Moreover, a treatment for treating impairment of neural plasticity through inhibition of GSK3b is provided as well as prevention of apoptosis of cells through inhibition of GSK3b.

10 Claims, 2 Drawing Sheets

METHODS AND PHARMACEUTICAL COMPOSITIONS FOR TREATING THE ANIMAL CENTRAL NERVOUS SYSTEM FOR PSYCHIATRIC DISORDERS

CROSS-REFERENCE TO RELATED APPLICATIONS

This is a non-provisional application claiming the benefit of and priority to U.S. provisional patent application No. 61/355,626 filed Jun. 17, 2010, which is incorporated herein by reference in its entirety.

BACKGROUND OF THE INVENTION

1. Field of the Invention

The present invention is directed to methods and pharmaceutical compositions for treating the animal central nervous system for psychiatric disorders, including mood disorders, depression, schizophrenia and frontal temporal dementia.

2. Description of the Related Art

Certain medical procedures, for example coronary artery bypass graft (CABG) surgery, are associated with neurological complications. In the case of CABG, the surgery is performed on more than 800,000 patients worldwide each year. Many of the CABG procedures performed are associated with neurological complications. These complications range from stroke in up to 16% of the patients to general cognitive decline with 50% of patients having impairment post-surgery and with progressive decline occurring in some patients over the next five years. In addition, physical and behavioral impairment manifest in some CABG patients. Newman M F et al., N. Eng. J. Med. 344:395-402 (2001); Brillman J., Neurol. Clin. 11:475-495 (1993); and Seines, O. A., Ann. Thorac. Surg. 67:1669-1676 (1999) are instructive.

Originally, it was hypothesized that the neurological complications associated with CABG surgery were either procedure or patient-related. The procedure generally implicated as potentially harmful was cardiopulmonary bypass using a pump and oxygenator. However, a recent study reports no difference in cognitive outcome between groups of patients undergoing CABG surgery performed with, or without, the pump and oxygenator. Such results suggest that the neurological impairments following CABG surgery may, in fact, be patient-related and, as a result, amenable to therapeutic manipulation.

In addition, patients at risk for, or diagnosed with disorders involving neurological impairments, e.g., Alzheimer's disease, Parkinson's disease, stroke, traumatic brain injury, spinal cord injury may benefit from similar therapeutic manipulation. See Crapper McLachlan, D. R., Dalton, A. J., Kruck, T. P. A., Bell, M. Y., Smith, W. L., Kalow, W., and Andrews, D. F. Intramuscular desferrioxamine in patients with Alzheimer's disease. The Lancet 337:1304-1308, 1991. Further, mood disorders such as bipolar disorder and depression, ADHD, schizophrenia and frontal temporal dementia are conditions that are generally in the category of neurological impairment with symptoms that may be amendable to therapeutic intervention.

GSK-3β (GSK3b) is a serine/threonine kinase that has diverse functions in various cellular activities in many cell types, including glycogen synthesis, cell survival and cell division. Unlike most protein kinases, GSK3b is constitutively active and its activity is down-regulated by upstream signals through inhibitory phosphorylation. The most important and well-known target of GSK3b is the β-catenin transcriptional coactivator. Active GSK3b can directly phosphorylate β-catenin, resulting in ubiquitination-mediated proteasomal degradation of β-catenin. The NF-AT transcription factor has been found to be another target of GSK-3β, at least in T cells and neurons. Different from the β-catenin phosphorylation, NF-AT phosphorylation mediated by GSK3b promotes its export from the nucleus, therefore terminating NF-AT-dependent transcription. The NF-AT activation is counterbalanced by GSK3b and $Ca^{2+}$-calcineurin. GSK3b phosphorylates NF-AT, leading to its nuclear export and transcriptional inactivation, while $Ca^{2+}$-calcineurin dephosphorylates NF-AT, leading to its nuclear import and transcriptional activation.

Thus, GSK3b is a unique serine/threonine kinase that is inactivated by phosphorylation to form phosphorylated GSK3b (pGSK3b). In response to insulin binding, PKB/AKT phosphorylates GSK3b on serine 9, which prevents GSKb from phosphorylating glycogen synthase. Unphosphorylated glycogen synthase is active and able to synthesize glycogen. GSK3b is also unique in that it requires a substrate that has been phosphorylated by a distinct kinase before it can phosphorylate the substrate. The phosphate priming mechanism explains why phosphorylation of serine 9 inactivates GSK3b. The phosphorylated serine binds to the GSK3b priming phosphate position and prevents binding of alternative substrates. In addition to insulin signaling, GSK3b participates in the Wnt signaling pathway, where it forms a complex with axin, beta-catenin and adenomatous polyposis coli (APC) protein. In the presence of Wnt, GSK3b is unable to phosphorylate beta-catenin, which leads to stabilization of beta-catenin.

Moreover, the Akt/GSK3 signaling pathway plays a significant role in responses to dopamine, 5-HT and psychotropic drugs, e.g., lithium, antidepressants and antipsychotics. Thus, this pathway and its diverse signaling molecules comprise important modulators of behavior. Regulation of this pathway by dopamine and 5-HT and three classes of psychotropic drugs (antipsychotics, mood stabilizers and antidepressants) indicates that Akt and GSK3 can act as signal integrators, allowing the precise coordination and cooperation of 5-HT and dopamine receptors signaling responses, with each other or with those related to other neutransmitters, hormones and/or growth factors. Thus, inhibition of GSK3b may provide a rationale for the effects of lithium, antidepressants and antipsychotics, which are often used in combination for various psychiatric conditions.

Studies suggest that inhibition of GSK3b may be a relevant target for the pathophysiology and treatment of psychiatric diseases including, e.g., bipolar disorder, also known as manic depression. A broader category of disease or condition may be termed mood disorders. Mood disorders include bipolar disorder, as well as patients experiencing major depression. Lithium is commonly used to treat mood disorders such as bipolar disorder and major depression and has been demonstrated to inhibit phosphorylation of GSK3b. In addition, valproic acid and electroconvulsive therapy also have been demonstrated to inhibit GSK3b. Studies convincingly demonstrate that GSK3b plays a critical role in depressive activity and the counteracting effects of antidepressants. Thus, the evidence indicates that inhibition of GSK3 contributes to the therapeutic action of these methods and agents. In addition, schizophrenia is associated with alterations in GSK3. See, e.g., Jope, "Glycogen Synthase Kinase-3 (GSK3) in Psychiatric Diseases and Therapeutic Interventions", Curr Drug Targets, 2006 Nov.; 7(11): 1421-1434, the contents of which are incorporated in their entirety. GSK3b clearly plays a role in these psychiatric diseases and conditions and inhibition of GSK3b, i.e., by phosphorylation, is of therapeutic value.

Further, GSK3b inhibitors are of considerable interest because they mimic the effect of insulin and may reduce the hyperphosphorylation of Tau that is observed in Alzheimer's disease. Moreover, GSK3b inhibits the xenobiotic and antioxidant cell response by direct phsphorylation and nuclear exclusion of the transcription factor Nrf2, and GSK3b is involved in hydrogen peroxide-induced suppression of Tcf/Lef-dependent transcriptional activity.

Moreover, GSK3b plays a central role in impairment of cell neural plasticity and cell death or apoptosis. Neural plasticity includes the capacity of cells to respond to stress or harmful agents. Experimentally, this may be measured by assessing the terminal outcome of stress-induced death by apoptosis. Impairment of neural plasticity and apoptosis driven by GSK3b exposure are implicated in a wide variety of diseases and/or conditions: exposure to growth factor withdrawal and inhibition of the phosphoinositide 3-kiase/Akt signaling pathway, mitochondrial toxins, hypoxia/ischemia, glutamate excitotoxicity, endoplasmic reticulum stress, DNA damage, ceramide, oxidative stress, Alzheimer's disease-related amyloid b-peptide, prion peptide, polyglutamine toxicity, HIV-associated conditions, hypertonic stress to name a few. The skilled artisan will recognize the full depth and breadth of the relevant diseases and/or conditions. Control of GSK3b by phosphorylation will reduce impairment of cell neural plasticity as well as apoptosis that may lead, inter alia, to non-lethal but nevertheless critical and stressful conditions in psychiatric disorders such as bipolar disorder, depression, dementia and schizophrenia.

Certain agents or compounds may increase or promote phosphorylation of GSK3b. A particular example of such an agent is deferoxamine (DFO), a hexadentate iron chelator.

In vivo studies have demonstrated that DFO increases phosphorylation status of GSK3b in HepG2 cells of the rat liver supplemented with fetal calf serum wherein DFO-induced iron depletion improved hepatic insulin resistance. DFO has also been shown to promote phosphorylation status of GSK3b and increased b-catenin protein in bone morphogenetic protein-2 (BMP-2)-treated mesenchymal stem cells (MSC). Such findings demonstrate that, inter alia, DFO may likewise regulate osteoblast differentiation of MSC through the b-catenin pathway, which plays a critical role in BMP-2-induced osteogenic differentiation.

These studies involving inhibition by DFO of GSK3b through phosphorylation are in vitro studies involving the liver and bone. These studies do not make obvious the possibility that DFO could be used to, e.g., treat psychiatric disorders within the brain and central nervous system for a variety of reasons.

For example, problems exist with the administration of DFO intravenously. DFO is not generally injected intravenously for at least three reasons. First, it is a small molecule and, as a result, is eliminated rapidly through the kidney. The typical plasma half-life in humans is less than 10 minutes. Second, the injection of an intravenous bolus of DFO causes acute hypotension that is rapid, may lead to shock and may be lethal. Third, intravenously or systemically administered DFO does not efficiently or effectively cross the blood-brain barrier. These characteristics have limited the utility of DFO in particular as a neuroprotective agent.

One published study administered DFO generally intranasally to iron overloaded patients. G. S. Gordon et al., Intranasal Administration of Deferoxamine to Iron Overloaded Patients, (1989) Am. J. Med. Sci. 297(5):280-284. In this particular study, DFO was administered to the patients as a nasal spray in a volume of 75 microliters per spray. Significantly, such sprays are known to deposit the drug or other substance in the lower third of the nasal cavity. This is verified by patient observations stating that a bad taste in the mouth was resulting from the drug passing through the nasopharynx and into the mouth. As a result, this study did not involve delivering the drug to the upper third of the nasal cavity. Thus, the drug would not have reached the olfactory epithelium or the olfactory nerves. As a result, delivery of the drug to the CNS would be less than optimal.

It is recognized that agent delivery to the CNS may occur along both the olfactory and trigeminal nerve pathways. See Thorne, RG (2004), Delivery of Insulin-Like Growth Factor-I to the Rat Brain and Spinal Cord Along Olfactory and Trigeminal Pathways Following Intranasal Administration, Neuroscience, Vol. 127, pp. 481-496. Optimal delivery taking advantage of both pathways is accomplished by administering the substance in the upper third of the nasal cavity.

It would be highly desirable to directly deliver an effective amount or dose of DFO to the upper one-third of the patient's nasal cavity, thereby bypassing the blood-brain barrier for treatment of diseases or conditions which are affected by non-phosphorylated GSK3b. As discussed, DFO stimulates phosphorylation of GSK3b, thereby inactivating or inhibiting GSK3b and thus therapeutic for patients suffering from certain psychiatric mood disorders (bipolar disorder and depression) as well as patients with schizophrenia and frontal temporal dementia. Therapy provided by the present invention, i.e., inactivation of GSK3b by DFO-stimulated phosphorylation of GSK3b may also be used to treat patients suffering from memory loss in a variety of conditions, including but not limited to Alzheimer's disease.

BRIEF SUMMARY OF THE INVENTION

The present invention comprises intranasal delivery of effective amounts of DFO directly to the CNS, in particular the brain treatments that inhibit GSK3b in patients with psychiatric disorders including, but not limited to, bipolar disorder, depression, ADHD and schizophrenia. In addition a treatment composition is disclosed which comprises DFO and in certain embodiments combines DFO with one or more of the psychotropic drug types, i.e., antipsychotics, mood stabilizers and antidepressants. Moreover, a treatment for treating impairment of neural plasticity through inhibition of GSK3b is provided as well as prevention of apoptosis of cells through inhibition of GSK3b.

The figures and the detailed description which follow more particularly exemplify these and other embodiments of the invention.

BRIEF DESCRIPTION OF THE DRAWINGS

The invention may be more completely understood in consideration of the following detailed description of various embodiments of the invention in connection with the accompanying drawings, which are as follows.

DETAILED DESCRIPTION OF THE INVENTION, INCLUDING THE BEST MODE

Figure 1A:
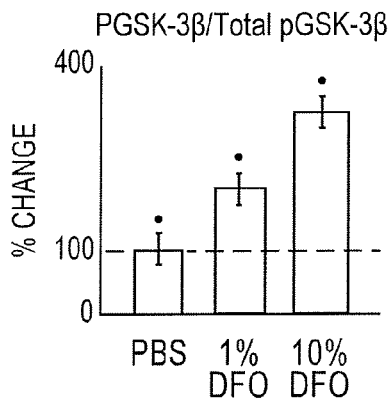
FIG. 1A is a bar graph illustrating the relative hippocampal concentrations of phosphorylated GSK3b as compared with total GSK3b when DFO is delivered to the upper third of the nasal cavity in C57 mice.

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

DEFINITIONS

As used herein, "central nervous system" (CNS) refers to the brain and spinal cord and associated tissues.

An "effective amount" of agent is an amount sufficient to prevent, treat, reduce and/or ameliorate the symptoms, neuronal damage and/or underlying causes of any of the referenced disorders or diseases. In some instances, an "effective amount" is sufficient to eliminate the symptoms of those diseases and overcome the disease itself.

In the context of the present invention, the terms "treat" and "treatment" and "therapy" and "therapeutic" and the like refer to alleviate, slow the progression, prophylaxis, attenuation or cure the referenced conditions or diseases and/or their associated symptoms.

"Prevent", as used herein, refers to putting off, delaying, slowing, inhibiting, or otherwise stopping, reducing or ameliorating the onset of the symptoms associated with the referenced diseases or conditions. The method of the present invention may be used with any animal, such as a mammal or a bird (avian), more preferably a mammal. Poultry are a preferred bird. Exemplary mammals include, but are not limited to rats, mice, cats, dogs, horses, cows, sheep, pigs, and more preferably humans.

Thus, methods and pharmaceutical compositions are described herein that, inter alia, treat patients with psychiatric disorders including, but not limited to, bipolar disorder, depression and schizophrenia by inhibition of GSK3b by administration of an effective amount of deferoxamine (DFO) to directly to the upper one-third of the patient's nasal cavity, thereby bypassing the blood-brain barrier. In addition a treatment composition is disclosed which comprises DFO and in certain embodiments combines DFO with one or more of the psychotropic drug types, i.e., antipsychotics, mood stabilizers and antidepressants. Moreover, a treatment for treating impairment of neural plasticity through inhibition of GSK3b is provided as well as prevention of apoptosis of cells through inhibition of GSK3b by administration of an effective amount of deferoxamine (DFO) to directly to the upper one-third of the patient's nasal cavity, thereby bypassing the blood-brain barrier.

An alternative to potentially lethal and generally ineffective intravenous injection of the metal chelator DFO may be accomplished using an alternative non-invasive method to directly target the substance to the central nervous system (CNS) and thus the brain under the present invention. Intranasal delivery allows substances to be rapidly delivered to the central nervous system, even those that do not readily cross the blood-brain barrier by bypassing the blood-brain barrier and directly exposes the CNS to the delivered substance. In this manner, unwanted systemic side effects are reduced if not eliminated.

Since DFO, similar to other metal chelators, has a strong Fe-III binding constant ($10^{31}$), it is rapidly eliminated from the blood and does not readily cross the blood-brain barrier. Thus, when metal chelator-based therapeutic agents are administered intravenously, orally or even intranasally—but not directly to the upper one-third of the nasal cavity—to target affected tissues within the brain, the therapeutic effect has been heretofore minimal. Delivery of intranasal DFO to the upper one-third of the nasal cavity has been assessed by administering 6 mg DFO bound to 6 μCi of $^{59}$Fe (as $^{59}$FeCl$_3$) to rats under anesthesia. The IN dose in 60 μL was administered as 6 μL drops over twenty minutes. Following delivery, tissues were removed for analysis. Using scintillation counting, labeled ferrioxamine was detected throughout the brain, with high concentrations detected in the olfactory bulbs, anterior olfactory nucleus, hypothalamus, frontal cortex and cervical spinal cord. Even higher ferrioxamine concentrations were observed in the trigeminal nerves and ventral dura. Peripheral tissues with the highest ferrioxamine concentrations included the olfactory epithelium, thyroid and cervical lymph nodes. By contrast, the blood concentrations of ferrioxamine, taken at 5 minute intervals from dosing up to 25 minutes post-dose, are quite low, indicating a minimization of exposure of the therapeutic agent to non-target tissue. The data provided in Table 1 below, thus illustrates that intranasal DFO, the concentrations having been calculated based on an extrapolation of the ferrioxamine concentration, administered to the upper one-third of the nasal cavity, is effectively delivered to the brain and upper spinal cord, with minimal systemic exposure.

Intranasal Delivery of DFO
(uM Concentrations in Tissues @ 25 Minutes after the Onset of Delivery)

TABLE 1

| uL delivered | 62 | 65 | 60 | 60 | 64 | 62 | 62 | 62 | 66 | 61 |
|---|---|---|---|---|---|---|---|---|---|---|
| uCi delivered | 36.55 | 38.40 | 35.45 | 35.35 | 36.77 | 35.28 | 35.30 | 34.72 | 35.80 | 34.31 |
| mg delivered | 6.15 | 6.44 | 5.95 | 5.95 | 6.29 | 6.05 | 6.05 | 6.07 | 6.45 | 6.00 |
| nmol delivered | 9,361.73 | 9,801.65 | 9,063.49 | 9,053.64 | 9,583.97 | 9,218.26 | 9,207.99 | 9,237.98 | 9,824.75 | 9,128.91 |
| Drug Delivery Time | 21 | 21 | 20 | 18 | 20 | 22 | 20 | 20 | 20 | 18 |
| Time of Perfusion | 25 | 25 | 26 | 27 | 25 | 26 | 27 | 26 | 26 | 26 |
| Rat weight | 303 | 302 | 264 | 281 | 298 | 309 | 336 | 283 | 318 | 315 |
| RAT # | DF09 | DF10 | DF11 | DF12 | DF13 | DF14 | DF15 | DF18 | DF19 | DF20 |
| Blood Sample 1 (5:00) | 1.2 | 1.6 | 0.6 | 1.2 | 0.7 | 1.5 | 1.1 | 0.8 | 0.3 | 1.8 |
| Blood Sample 2 (10:00) | 1.1 | 2.1 | 1.1 | 1.2 | 1.2 | 1.8 | 1.7 | 1.0 | 0.4 | 1.9 |

TABLE 1-continued

| | | | | | | | | | | |
|---|---|---|---|---|---|---|---|---|---|---|
| Blood Sample 3 (15:00) | 1.1 | 2.0 | 0.5 | 1.8 | 0.9 | 1.4 | 1.7 | 1.3 | 0.5 | 2.6 |
| Blood Sample 4 (20:00) | 1.1 | 1.8 | 0.3 | 1.9 | 1.1 | 1.6 | 1.5 | 1.1 | 0.4 | 2.9 |
| Blood Sample 5 (25:00) | 1.8 | 1.6 | 1.8 | 1.3 | 1.5 | 2.2 | 1.7 | 1.3 | 0.5 | 2.1 |
| Superficial Nodes (4) | 3.4 | 0.9 | 0.6 | 0.9 | 2.2 | 0.6 | 1.8 | 0.6 | 1.1 | 0.8 |
| Cervical Nodes (2) | 12.9 | 10.9 | 34.2 | 40.8 | 58.2 | 51.4 | 65.1 | 13.2 | 11.4 | 8.1 |
| Dorsal Dura | 26.5 | 11.4 | 7.4 | 14.1 | 16.6 | 32.0 | 8.0 | 5.9 | 35.8 | 5.1 |
| Ventral Dura | 25.3 | 38.7 | 70.9 | 17.7 | 58.3 | 44.0 | 51.5 | — | 62.8 | 11.6 |
| Trigeminal Nerve | 33.3 | 14.7 | 22.4 | 8.4 | 72.8 | 25.1 | 26.6 | 17.4 | 27.0 | 9.5 |
| Olfactory Bulbs | 12.7 | 10.6 | 30.0 | 14.7 | 20.5 | 13.1 | 28.0 | 27.5 | 21.6 | 6.6 |
| Anterior Olfactory Nucleus | 4.4 | 4.2 | — | — | 5.4 | 2.5 | 5.5 | 4.4 | 7.7 | — |
| Frontal Cortex | 4.3 | 3.3 | 13.6 | — | 2.5 | 1.1 | 6.5 | 1.4 | 5.0 | — |
| Caudate/Putamen | 2.0 | 1.5 | 2.1 | — | 2.4 | 0.9 | 1.6 | 1.1 | 2.0 | — |
| Septal Nucleus | 2.6 | 1.6 | 1.6 | — | 3.2 | 1.9 | 2.0 | 1.8 | 2.9 | — |
| Hippocampus | 0.9 | 0.9 | 0.9 | — | 2.3 | 1.2 | 1.2 | 0.5 | 1.3 | — |
| Parietal cortex | 1.3 | 1.6 | 2.3 | — | 0.7 | 1.9 | 2.8 | 0.8 | 1.0 | — |
| Thalamus | 1.1 | 1.2 | 1.2 | — | 1.5 | 1.0 | 1.0 | 0.8 | 1.2 | — |
| Hypothalamus | 5.4 | 7.3 | 6.5 | — | 3.1 | 3.0 | 6.1 | 2.7 | 3.8 | — |
| Midbrain | 1.3 | 1.3 | 1.1 | — | 1.8 | 1.3 | 1.2 | 0.6 | 1.3 | — |
| Pons | 2.0 | 1.5 | 1.4 | — | 1.5 | 2.0 | 2.6 | 0.7 | 2.4 | — |
| Medulla | 1.1 | 2.3 | 1.2 | — | 1.7 | 2.2 | 3.0 | 1.0 | 2.0 | — |
| Upper Cervical Spinal Cord | 2.1 | 1.4 | 3.7 | 1.5 | 3.9 | 6.8 | 7.3 | 1.4 | 4.6 | 4.6 |
| Cerebellum | 0.8 | 0.9 | 0.6 | — | 0.9 | 1.4 | 1.1 | 0.5 | 1.1 | — |
| Thyroid | 1125.4 | 2932.7 | 448.2 | 814.1 | 466.7 | 1285.4 | 753.3 | 751.4 | 3463.9 | 605.9 |
| Olfactory Epithelium | 12016.8 | 11374.8 | 11191.7 | 13841.7 | 9519.2 | 10724.4 | 11764.8 | 9572.8 | 9321.0 | 12205.2 |
| Axillary Nodes (2) | 0.5 | 0.4 | 0.3 | 0.3 | 0.4 | 0.5 | 0.3 | 0.4 | 1.0 | 3.1 |
| Liver | 0.4 | 0.8 | 0.4 | 0.3 | 0.3 | 0.3 | 0.3 | 0.4 | 0.4 | 0.4 |
| Kidney | 1.0 | 0.4 | 0.5 | 0.6 | 0.4 | 0.2 | 0.6 | 1.0 | 1.2 | 0.5 |
| Muscle | 0.4 | 0.3 | 0.3 | 0.4 | 0.4 | 0.2 | 0.6 | 0.6 | 0.7 | 0.4 |
| Heart | 0.4 | 0.4 | 0.5 | 1.6 | 0.6 | 0.3 | 2.2 | 0.2 | 0.2 | 0.5 |
| Lung | 0.6 | 1.4 | 0.7 | — | 1.0 | 0.5 | 2.2 | 1.5 | 1.1 | 0.5 |
| Lower Cervical Spinal Cord | 0.5 | 5.3 | 1.0 | 2.7 | 0.3 | 0.1 | 3.8 | 0.4 | 1.8 | 0.3 |
| Thoracic Spinal Cord | 0.1 | 0.2 | 0.2 | 0.4 | 0.1 | 0.1 | 1.2 | 0.3 | 0.6 | 0.1 |
| Lumbar Spinal Cord | 0.1 | 0.1 | 0.1 | 0.1 | 0.1 | 0.7 | 0.1 | 0.1 | 0.1 | 0.1 |
| Spinal Dura | 1.9 | 3.3 | 1.3 | 4.2 | 1.1 | 2.3 | — | 0.4 | 1.5 | 0.8 |

The method of the invention delivers DFO to the upper third of the nasal cavity of a mammal. It is preferred that the agent be delivered to the olfactory area in the upper one-third of the nasal cavity and, particularly, to the olfactory neuroepithelium in order to promote rapid and efficient delivery of the agent to the CNS along the olfactory neural pathway rather than the capillaries within the respiratory epithelium. The preferred transport of the DFO to the brain by means of the olfactory and trigeminal neural pathways rather than the circulatory system so that the harmful side effects and potentially short half-life of the agent is not an issue. The preferred method allows direct delivery of DFO to the brain. The data provided in Table 1 above strongly supports the increased efficacy of one embodiment of this element of the inventive method.

To deliver an effective amount of DFO directly to the brain, DFO is, either alone or in combination with other substances, e.g., psychotropic agents, mood stabilizers such as lithium and/or antipsychotic agents as a pharmaceutical composition, may be administered to the olfactory area located in the upper one-third of the nasal cavity. The composition may be administered intranasally as a powered or liquid spray, nose drops, a gel or ointment, through a tube or catheter, by syringe, packtail, pledget or by submucosal infusion. Optimization of the administration of DFO is provided by the various embodiments by applying DFO to the upper third of the nasal cavity.

The optimal concentration of DFO will necessarily depend upon the characteristics of the patient and the nature of the disease or condition for which the agent is being used and the frequency of administration. In addition, the concentration will depend upon whether DFO is being employed in a preventive or treatment capacity. Further, the stage of a particular disease or disorder may dictate the optimal concentration of the agent.

Figure 1B:
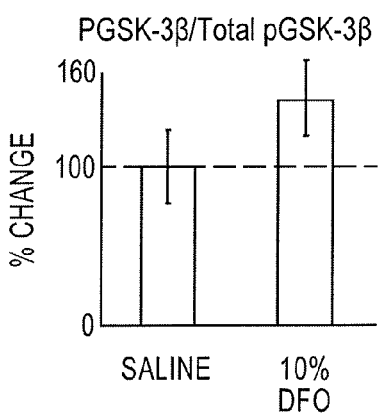
FIG. 1B is a bar graph illustrating the relative hippocampal concentrations of phosphorylated GSK3b as compared with total GSK3b when DFO is delivered systemically in C57 mice.

Having established that administration of DFO to the upper one-third of the nasal cavity is a highly effective and efficient targeting methodology for regions of the brain and CNS as opposed to systemic exposure, we now turn to further exemplary work performed according to one embodiment of the inventive method the results of which are illustrated in FIGS. 1A and 1B. This study firmly demonstrates that administration of DFO to the upper one-third of the nasal cavity results in an increase in phosphorylated GSK-3b as compared with total GSK-3b.

The study method providing results in FIGS. 1A and 1B comprised normal C57 mice which were treated with DFO by administration to the upper third of the nasal cavity, thereby delivering the DFO directly to the CNS by bypassing the blood-brain barrier. Treatment groups consisted of 1% DFO, 10% DFO and saline. Mice were treated five days/week for four weeks. Mice were then dosed a final time, euthanized after 30 minutes, brain tissues collected an analyzed for biochemical changes. Protein extraction was achieved by homogenization of frozen brain tissues in 5 volumes of ice-cold RIPA buffer supplemented with protease inhibitor cocktail and phosphatase inhibitor cocktail. Homogenates were centrifuged at 20,000×g for 20 minutes at 4C. Supernatant was collected from the cortex, diencephalon and hippocampus and stored at −70C until analysis by western blot and ELISA.

The results of the study are reflected in FIG. 1A. Both groups of DFO mice (1% and 10%) had a significantly greater ratio of phosphorylated GSK3b (pGSK3b) to GSK3b. 1% DFO mice had a 99.8% higher ratio of pGSK3b/GSK3b than PBS mice. 10% DFO mice had a 214% higher ratio of pGSK3b/GSK3b than PBS mice. Further, the 10% DFO mice had a significantly higher ratio (57.4%) of pGSK3b/GSK3b than the 1% DFO mice. Significantly, a dose response of DFO brain concentration is clearly evident.

FIG. 1B illustrates the effect of DFO administered systemically, and provided no statistical change in the ratio of pGSK3b/GSK3b.

Figure 2A:
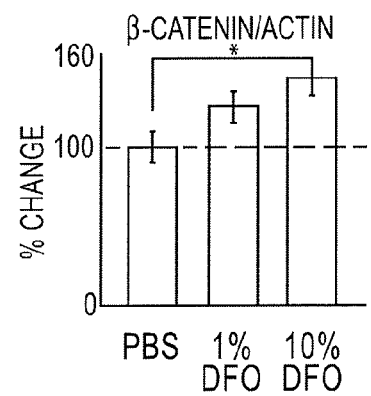
FIG. 2A is a bar graph illustrating the relative hippocampal concentrations of beta-Catenin/Actin when DFO is delivered to the upper third of the nasal cavity in C57 mice.
Figure 2B:
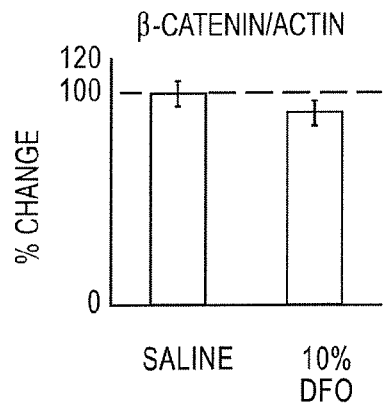
FIG. 2B is a bar graph illustrating the relative hippocampal concentrations of beta-Catenin/Actin when DFO is delivered systemically in C57 mice.

Turning now to FIG. 2A, beta-Catenin/Actin brain concentrations are evaluated according to the previously described method after administration of 1% and 10% DFO to the upper third of the nasal cavity. The concentrations of beta-Catenin/Actin in the hippocampus provide a similar dose response to that of the pGSK3b/GSK3b seen in FIG. 1A. Moreover, the systemic delivery of DFO did not significantly alter levels of beta-Catenin/Actin as seen in FIG. 2B.

Figure 3:
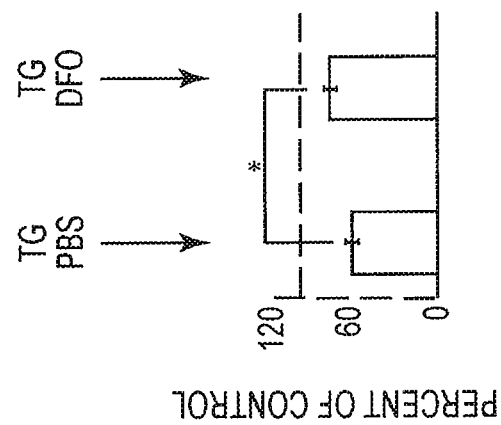
FIG. 3 is a bar graph illustrating relative whole brain concentrations of phosphorylated GSK3b as compared with total GSK3b when DFO is delivered to the upper third of the nasal cavity in tau mice (P301L model of accumulating hyperphosphorylated tau).
Figure 3:
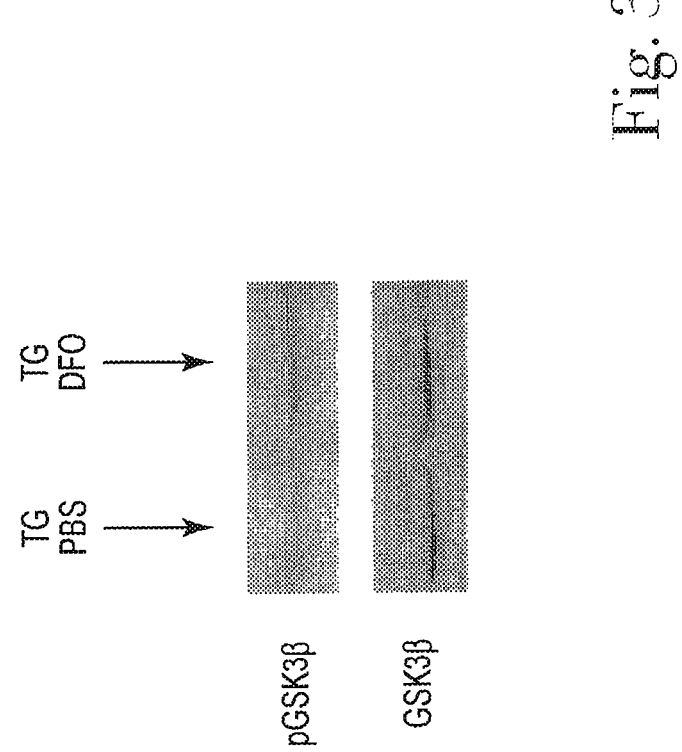

FIG. 3 illustrates the ratio of whole brain concentrations of pGSK3b/GSK3b in tau mice when 1% and 10% DFO is administered to the upper third of the nasal cavity. The results are consistent with FIG. 1A, e.g., in that a significant increase is observed with DFO treatment of tau mice.

In another embodiment of the present invention, a pharmaceutical composition comprised of DFO and the group consisting of: mood stabilizers, e.g., lithium, antidepressants, and antipsychotics may be administered to treat bipolar disorder, depression, frontal temporal dementia, ADHD and/or schizophrenia. The antidepressants in the various embodiments, methods and pharmaceutical compositions, of the present invention may comprise drugs in the categories: serotonin reuptake inhibitors; serotonin-norepinephrine reuptake inhibitors; noradrenergic and specific serotonergic antidepressants, norepinephrine (noradrenaline) reuptake inhibitors; norepinephrine-dopamine reuptake inhibitors; serotonin reuptake enhancers; norepinephrine-dopamine disinhibitors; tricyclic antidepressants; monoamine oxidase inhibitors and augmenter drugs. The skilled artisan will recognize various agents within these categories, each of which may be candidates for various pharmaceutical compositions and/or method of the present invention.

Further, the antipsychotics in the various embodiments, methods and pharmaceutical compositions of the present invention may comprise drugs in the following categories: Butyrophenones, Phenothiazines, Thioxanthenes as well as Clozapine, Olanzapine, Reisperidone, Quetiapine, Ziprasidone, Amisulpride, Asenapine, Paliperidone, Iloperidone, Zotepine, Sertindole and others well known to the skilled artisan.

In another embodiment of the present invention, a method and pharmaceutical composition comprising DFO may be provided for administration to the upper third of the patient's nasal cavity to treat GSK-3-promoted apoptosis in the CNS, particularly in the brain wherein the apoptosis results from non-phosphorylated GSK-3b. The DFO inhibits phosphorylation of GSK3b, thereby inactivating GSK-3b and preventing apoptosis or cell death as a result.

In another embodiment of the present invention, a method and pharmaceutical composition comprising DFO may be administered to the upper third of the patient's nasal cavity to treat central nervous system cells of impairment of neural plasticity caused by GSK-3. The DFO inhibits phosphorylation of GSK3b, thereby inactivating GSK3b and preventing neural plasticity as a result.

An effective amount, as herein defined, of DFO to be administered pursuant to embodiments of the invention is the most preferred method of expression of dosage. Such effective amount is dependent upon many factors, including but not limited to, the type of disease or condition giving rise to an anticipated cerebral ischemic episode, the patient's general health, size, age, and the nature of treatment, i.e., short-term of chronic treatment. For illustrative purposes only, exemplary treatment regimens relating generally to DFO as disclosed herein, including dosage ranges, volumes and frequency are provided below:

Efficacious dosage range: 0.0001-1.0 mg/kg.

A more preferred dosage range may be 0.005-1.0 mg/kg.

The most preferred dosage range may be 0.05-1.0 mg/kg.

The dosage volume (applicable to nasal sprays or drops) range may be 0.015 ml-1.0 ml.

The preferred dosage volume (applicable to nasal sprays or drops) range may be 0.03 ml-0.6 ml.

Generally, the treatment may be given in a single dose or multiple administrations, i.e., once, twice, three or more times daily over a period of time. The brain concentrations that are likely to be achieved with the dosage ranges provided above are, for a single dose: 0.1 nM-50 $\mu$M. Over the course of a multi-dose treatment plan, the maximum brain concentration may be as high as 500 $\mu$M.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:

1. A method to treat patients with bipolar disorder, depression, ADHD, or schizophrenia comprising:
   administering at least one effective dose of deferoxamine (DFO) to the upper one-third of the patient's nasal cavity;
   inhibiting GSK-3b in the patient's brain; and
   treating the patient with bipolar disorder, depression, ADHD, or schizophrenia.

2. The method of claim 1, wherein the inhibiting of GSK-3b in the patient's brain results from phosphorylation of the GSK-3b.

3. The method of claim 2, wherein the at least one effective dose is within the range of 0.0001-1.0 mg/kg and which provides a brain concentration within the range of 0.1 nM-50 $\mu$M.

4. The method of claim 1, further comprising administering an effective dose of the group consisting of a mood stabilizer, an antidepressant and an antipsychotic agent.

5. A method for protecting central nervous system cells from GSK-3-promoted apoptosis, comprising:
   administering at least one effective dose of deferoxamine (DFO) to the upper one-third of the patient's nasal cavity;
   inhibiting GSK-3b in the patient's brain; and
   protecting central nervous system cells from GSK-3-promoted apoptosis.

6. The method of claim 5, wherein the inhibiting of GSK-3b in the patient's brain results from phosphorylation of the GSK-3b.

7. The method of claim 6, wherein the at least one effective dose is within the range of 0.0001-1.0 mg/kg and which provides a brain concentration within the range of 0.1 nM-50 $\mu$M.

8. A method for treating central nervous system cells of impairment of neural plasticity caused by GSK-3, comprising:
   administering at least one effective dose of deferoxamine (DFO) to the upper one-third of the patient's nasal cavity;
   inhibiting GSK-3b in the patient's brain; and treating the central nervous system cells for impairment of neural plasticity caused by GSK-3.

9. The method of claim 8 wherein the inhibiting of GSK-3b in the patient's brain results from phosphorylation of the GSK-3b.

10. The method of claim 8, wherein the at least one effective dose is within the range of 0.0001-1.0 mg/kg and which provides a brain concentration within the range of 0.1 nM-50 µM.

* * * * *